United States Patent [19]

Sams

[11] 4,085,739
[45] Apr. 25, 1978

[54] ELECTROENCEPHALOGRAPH CAP AND ELECTRODE HARNESS

[76] Inventor: Marvin W. Sams, P.O. Box 3515, Toledo, Ohio 43608

[21] Appl. No.: 743,571

[22] Filed: Nov. 22, 1976

[51] Int. Cl.² .............................................. A61B 5/04
[52] U.S. Cl. ............................. 128/2.1 B; 128/2.1 E; 128/410; 128/DIG. 4
[58] Field of Search ................. 128/2.1 E, 2.1 B, 380, 128/410, 418, DIG. 4; 2/171.2, 421

[56] References Cited

U.S. PATENT DOCUMENTS

| 3,148,375 | 9/1964 | Jones | 2/421 |
| 3,490,439 | 1/1970 | Rolston | 128/2.1 E |
| 3,534,727 | 10/1970 | Roman | 128/DIG. 4 X |
| 3,658,054 | 4/1972 | Iberall | 128/2.1 B X |
| 3,925,822 | 12/1975 | Sawyer | 2/421 |
| 3,998,213 | 12/1976 | Price | 128/2.1 B |
| 4,016,868 | 4/1977 | Allison | 128/2.1 E |

Primary Examiner—Robert W. Michell
Assistant Examiner—Lee S. Cohen
Attorney, Agent, or Firm—Marshall & Yeasting

[57] ABSTRACT

A flexible cap incorporating electrodes of an electroencephalographic apparatus is firmly held in place on a patient's head without inducing a muscular reaction by a pair of criss cross elastic straps connecting the cap to a band encircling the patient's body, the criss cross straps being attached to the cap so that the resultant force of the cap is directed approximately through the joint between the patient's skull and spinal column.

5 Claims, 2 Drawing Figures

ELECTROENCEPHALOGRAPH CAP AND ELECTRODE HARNESS

BACKGROUND OF THE INVENTION

It has been a problem to provide accurate positioning and holding the electrodes of an electroencephalographic apparatus in operative contact with a patient's scalp without inducing a muscular reaction that interferes with brain potentials of interest. Activity of the facial or neck muscles produces electrical voltages or potentials that add to the potentials appearing on the scalp as a result of brain activity and thus produce false or interfering signals. To position the electrodes it has been proposed to mount the electrodes in a rigid helmet-like cap that is placed on the patient's head. This is unsatisfactory because of the variations in skull shape and size from patient to patient and the difficulty of getting uniform pressure on the various electrodes. The misfits usually resulted in patient discomfort and muscular reactions. It has also been proposed to use a flexible cap arrangement with a hold down strap under the patient's chin or lower jaw. If the strap is tight enough to hold the cap and electrodes firmly in place it is annoying to the patient and induces a muscular reaction in the facial and jaw muscles and thus unwanted or interfering electrical potentials.

SUMMARY OF THE INVENTION

According to the invention a flexible cap containing electroencephalographic (EEG) electrodes is held in place by straps connected to a harness secured to the patient's trunk. The harness straps are attached to the cap and directed to the harness in such a manner that tension forces in the straps pulling the cap down onto the patient's head do not induce a muscular reaction in the patient. Preferably the harness comprises elastic straps each extending from a side of the cap across the patient's throat to the opposite side of a chest strap encircling the patient's body at the level of the armpits. Since the elastic straps cross each other from side to side there is little net change in force as the patient tilts his head from side to side. Also, since the elastic straps cross anteriorly of the backbone and the patient is either leaning back in a chair or reclining the tension force of the straps partially relieves the tension in the neck muscles or head pressure against a chair back or other support. In any event, the cap is held securely in place without inducing any muscular reaction in head or neck muscles that might generate spurious potentials at the electrodes.

DESCRIPTION OF A PREFERRED EMBODIMENT

Figure 1:
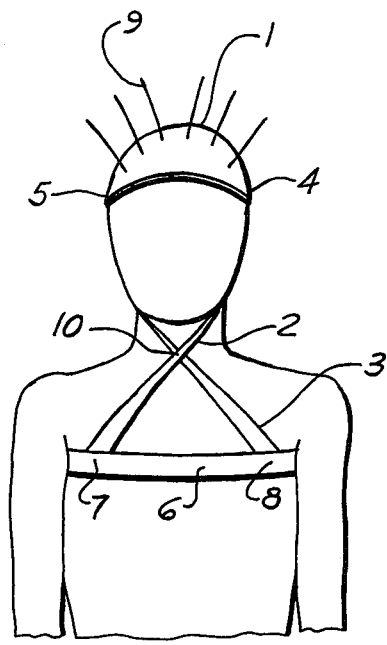
FIG. 1 is a head and shoulders front view of a patient to whom an electroencephalographic cap has been applied.

The preferred arrangement of a harness to hold an electrode cap in position is illustrated in the drawings.

Referring to the drawings a cap 1 formed of a flexible substantially stretchable material is held in place by a pair of elastic straps 2 and 3 attached to sides 4 and 5 of the cap 1 and extending to and connected to a harness band 6. As shown, the elastic strap 2 extends from the left side 4 of the cap 1 (as it is positioned on the patient's head) under the patient's chin, and is attached to the harness band 6 at a point 7 located just ahead of the patient's right arm pit. Similarly the other elastic strap 3 extends from the right side 5 of the cap to a point 8 on the harness band in front of the patient's left arm pit.

The harness band 6 is preferably made of a strip of an elastic material to which strips of "Velcro" (a releasable fastening material having mating areas comprising a large number of miniature plastic or metal hooks inter-engaging the hooks of the mating piece) are attached to provide an easy method of fastening the ends of the band together with a proper tension in the band. Other means, such as a conventional belt buckle, can also be used. Likewise mating pieces of Velcro may be incorporated in the lower ends of the elastic straps 2 and 3 and to the harness band 6 at the points or areas 7 and 8 to connect the straps 2 and 3 to the band 6.

The cap 1 is fitted with electrodes, not shown, each of which is connected to a terminal lead 9 adapted to be connected to the electronic portions of the E.E.G. apparatus.

Figure 2:
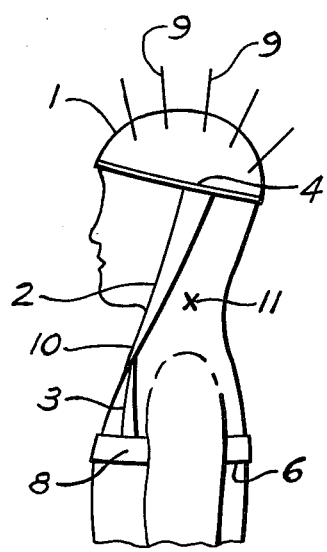
FIG. 2 is a head and shoulders side view of the patient and cap shown in FIG. 1.

The important feature is that the elastic straps 2 and 3 exert no substantial force against the patient's face or against his neck. Furthermore, a crossing point 10 of the straps 2 and 3 is located as close as possible to skeletal joint between the patient's skull and backbone as approximately indicated by a point 11 in FIG. 2.

If the patient is tilted back in a chair or is reclining his head tends to tip backward thus tensioning the elastic straps 2 and 3 without the exertion of any muscular action by the patient. The minimization of muscular exertion by the patient particularly in the face and neck muscles greatly reduces the extraneous voltages appearing at the electrodes and thus permits greater accuracy in detecting brain activity.

I claim:

1. A harness for holding electrodes in contact with selected points on a patient's head while obtaining electroencephelographic data, said harness comprising, in combination, a cap of flexible material and size to loosely fit a patient's head, a plurality of electrodes mounted at selected points in said cap and arranged to contact the patient's scalp, a harness band of sufficient length to encircle the patient's body below the armpits, and a pair of elastic straps attached to and extending from lateral portions of the cap in criss-cross manner to said harness band, whereby the cap is held firmly in place without inducing muscular reaction or inhibiting free movement of the patient's head.

2. A harness according to claim 1 in which the cap is constructed of a flexible substantially stretchable material.

3. A harness according to claim 1 in which the harness band is elastic, and adjustable fastener means on the harness band whereby the band may be readily adjusted to the patient's body.

4. A harness according to claim 1 in which said pair of straps are independent of each other.

5. A harness according to claim 1 in which the elastic straps are attached to the sides of the cap at points generally midway between the front and back of the cap.

* * * * *